United States Patent [19]

Lareginie et al.

[11] Patent Number: 5,936,016
[45] Date of Patent: Aug. 10, 1999

[54] PHOTOCHROMIC COMPOUNDS AND METHODS FOR THEIR USE

[75] Inventors: Pierre Lareginie; Vladimir Lokshin; André Samat; Robert Guglielmetti, all of Marseille, France; Elena Zaballos Garcia, Puerto de Sagunto, Spain

[73] Assignee: Essilor International Compagnie Generale D'Optique, Charenton Cedex, France

[21] Appl. No.: 08/776,025

[22] PCT Filed: Jul. 31, 1995

[86] PCT No.: PCT/FR95/01031

§ 371 Date: Jan. 23, 1997

§ 102(e) Date: Jan. 23, 1997

[87] PCT Pub. No.: WO96/04590

PCT Pub. Date: Feb. 15, 1996

[30] Foreign Application Priority Data

Jul. 29, 1994 [FR] France .................................. 94 09449

[51] Int. Cl.$^6$ .............................. C08K 5/34; G02C 7/10; C07D 265/00
[52] U.S. Cl. ............................ 524/94; 252/586; 351/163; 359/885; 544/71
[58] Field of Search ............................... 524/94; 252/586; 351/163; 359/885; 544/71

[56] References Cited

U.S. PATENT DOCUMENTS

| | | |
|---|---|---|
| 3,578,602 | 5/1971 | Ono et al. ................................ 252/587 |
| 4,286,957 | 9/1981 | Le Naour-Sene . |
| 4,342,668 | 8/1982 | Hovey et al. ............................ 252/586 |
| 4,880,667 | 11/1989 | Welch . |
| 4,931,220 | 6/1990 | Haynes et al. ............................. 524/94 |
| 5,000,878 | 3/1991 | Chu ......................................... 350/354 |
| 5,114,621 | 9/1992 | Guglielmetti . |
| 5,139,707 | 8/1992 | Guglielmetti . |
| 5,446,151 | 8/1995 | Rickwood et al. ....................... 544/71 |

FOREIGN PATENT DOCUMENTS

| | | |
|---|---|---|
| 245020 | 11/1987 | European Pat. Off. . |
| 316980 | 5/1989 | European Pat. Off. . |
| 63-175094 | 7/1988 | Japan . |
| 63-250381 | 10/1988 | Japan . |
| 63-275587 | 11/1988 | Japan . |
| 64-30744 | 2/1989 | Japan . |
| 1-170904 | 7/1989 | Japan . |
| 2-243694 | 9/1990 | Japan . |
| 3-66692 | 3/1991 | Japan . |
| 3-81278 | 4/1991 | Japan . |
| 03-251587 | 11/1991 | Japan . |
| 3251587 | 11/1991 | Japan . |

*Primary Examiner*—Veronica P. Hoke
*Attorney, Agent, or Firm*—Arnold White & Durkee

[57] ABSTRACT

The present invention relates to photochromic compounds of spiro[indoline[2,3']-naphthoxazine] structure, characterized in that they contain, in the 6' position, a group $R_6$ chosen from the following groups: cyano and phenylsulfonyl linked via the sulfur atom to carbon 6', and methods of using such compounds.

15 Claims, 5 Drawing Sheets

PHOTOCHROMIC COMPOUNDS AND METHODS FOR THEIR USE

FIELD OF THE INVENTION

The invention relates to novel photochromic compounds of spiro[indoline[2,3']benzoxazine] with a 6' cyano or phenylsulfonyl group and containing a 7',8'-fused benzene ring on the benzoxazine nucleus, and to their use in the ophthalmic optics field, in particular in and/or on ophthalmic lenses.

BACKGROUND OF THE INVENTION

Photochromism is a phenomenon which has been known for many years. A compound is said to be photochromic when, after irradiation with a beam of light, certain wavelengths of which are in the ultraviolet region, this compound changes color and returns to its original color as soon as the irradiation ceases.

There are many applications of this phenomenon, but one of the more particularly advantageous known applications relates to the ophthalmic optics field.

Such compounds can be used in the manufacture of lenses or spectacle lens glasses for the purpose of screening light radiation as a function of its intensity.

The incorporation of photochromic compounds into an organic material constituting an ophthalmic lens makes it possible to obtain a lens glass whose weight is considerably reduced when compared with conventional lenses made of inorganic glass, which contain silver halides as photochromic agents. Their incorporation into organic materials has always posed technical difficulties.

However, any compound with photochromic properties cannot necessarily be used in the ophthalmic optics field. The reason for this is that the photochromic compound must satisfy a certain number of criteria, including, inter alia:

a high colorability, which is a measurement of the capacity of a photochromic compound to have an intense color after isomerization;

a coloration after light absorption making the photochromic compound suitable, alone or in combination with other photochromic compounds to be used in ophthalmic glasses or lenses;

an absence of coloration or very weak coloration in the initial form;

rapid coloration or decoloration kinetics;

a photochromism which manifests itself over the widest possible temperature range, and in particular preferably between 0 and 40° C.

The known and currently used organic photochromic compounds generally have a decreasing photochromism when the temperature increases, such that the photochromism is particularly pronounced at temperatures close to 0° C., whereas it is much weaker, or even nonexistent, at temperatures of about 40° C., these being temperatures which lens glasses may reach, in particular during exposure to the sun.

Another problem encountered for the photochromic compounds of the prior art is their lifetime. Indeed, for certain products of the prior art, a relatively short lifetime is observed. The reason for this is that after a certain number of coloration and decoloration cycles, the compound no longer has reversible photochromic properties.

The photochromic properties of spiroxazines have been described by R. E. Fox in the document Final Report of Contact AF 41, A.D. 440226 1961. 657.

Compounds of the spiro (indoline-naphthoxazine) type have been synthesized and described in particular in the article by N. Y. C. Chu "Photochromism: Molecules and Systems" Ed. H. Dürr, H. Bovas Laurent, Elsevier, Amsterdam 1990, ch. 24, as well as compounds of the spiro (indoline-quinazolinoxazine) or spiro(indoline-benzothiazoloxazine) type in U.S. Pat. Nos. 5,139,707 and 5,114,621 (R. Guglielmetti, P. Tardieu) granted in the name of the company Essilor.

Compounds of the photochromic spiro[indoline-[2,3'] benzoxazine] type have also been synthesized and described in patent application EP-0,245,020.

Japanese patent application JP 3,251,587 moreover discloses photochromic compounds of the indolinospiropyridobenzoxazine type bearing, in the 6' position of the benzoxazine nucleus, CN, $CF_3$ or alkoxycarbonyl groups, and the indoline nitrogen of which is substituted with alkoxycarbonylalkyl groups.

These compounds are photochromic at temperatures of about from 30 to 40° C.

These compounds, in their open form, have an absorption spectrum in the visible region containing an absorption maximum at a wavelength $\lambda_{max}$ ranging from 600 to 617 nm.

It is desirable to obtain compounds whose absorption spectrum in the visible region, for their open form, contains an absorption maximum at wavelengths higher than those of the compounds of patent application JP 3,251,587.

Indeed, shifting of the $\lambda_{max}$ value to higher values leads to photochromic compounds of color approaching green in their open form, this color being desired for ophthalmic use.

SUMMARY OF THE INVENTION

The Applicant has discovered a novel family of compounds of spiro[indoline[2,3']benzoxazine] structure with a cyano or phenylsulfonyl group in the 6' position and containing a 7',8'-fused benzene ring on the benzoxazine nucleus, this family of compounds having particularly advantageous photochromic properties.

Indeed, the compounds of the invention have a high colorability, in their open form, in the visible region. They have green-blue colorations. They can therefore be used with other photochromic compounds giving a red color in order to obtain a natural coloration when exposed to light.

The compounds in accordance with the invention, in their colored form, show a shift towards higher wavelengths of the absorption spectrum in the visible region when compared with homologous compounds of the prior art of spiro[indoline[2,3']benzoxazine] structure not substituted in the 6' position or of spiro[indoline[2,3']benzoxazine] structure substituted in the 6' position, of application JP 3,251,587. The wavelengths corresponding to the absorption maximum are greater than 630 nm and usually greater than 640 nm.

The compounds according to the invention have strong absorption bands in the region of visible UV radiation, in their closed form, as well as a shift towards longer wavelengths for the absorption bands of the UV spectrum of the closed form when compared with the spiro[indoline[2,3'] benzoxazine] homologues not substituted in the 6' position, of the prior art.

Since most of the UV radiation is blocked by conventional panes of glass, with the exception of visible UV radiation, the compounds of the invention are therefore of good colorability even if a pane of glass is placed between the source of UV radiation (natural light) and the photochromic compound.

The compounds in accordance with the invention moreover have an absence of coloration or a very weak coloration in the initial state and rapid coloration and decoloration kinetics over a wide temperature range, in particular between 0 and 40° C. Their photochromic properties are noteworthy both at temperatures of about 20° C. and at temperatures of about 35° C. The result of this is that they are particularly suitable for contact lenses whose temperature of use is about 35° C. and for spectacle lens glasses during exposure to the sun.

The Applicant has also observed that these compounds have a particularly long lifetime.

The effect of all these properties is to make these novel photochromic compounds particularly advantageous in their use in ophthalmic optics and in particular for their use in and/or on ophthalmic lenses.

For the purposes of the invention, ophthalmic lenses refers to spectacle lens glasses, in particular lenses of sunglasses and contact lenses.

One subject of the invention thus consists of the novel photochromic compounds.

Another subject of the invention consists of their use in ophthalmic optics.

The subject of the invention is also compositions intended to be used for coating ophthalmic lenses or their incorporation into these lenses.

Other subjects of the invention will become apparent on reading the description and the examples which follow.

DETAILED DESCRIPTION OF THE INVENTION

The photochromic compounds in accordance with the invention are compounds of spiro[indoline[2,3'] benzoxazine] structure essentially characterized in that they are substituted in the 6' position with a group $R_6$ which is a cyano group or a phenylsulfonyl group attached via the sulfur atom to carbon 6', and possess a 7',8'-fused benzene ring on the benzoxazine nucleus.

In the present invention, the term phenylsulfonyl group is understood to refer to the phenylsulfonyl radical and any derivative thereof, and in particular substituted phenylsulfonyl radicals.

The photochromic compounds in accordance with the invention are preferably chosen from those corresponding to formula (I) below:

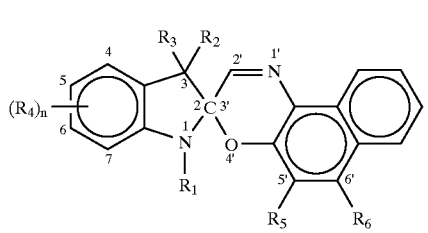

(I)

in which:

n ranges from 0 to 4;

$R_1$ represents:
  i) an alkyl group of 1 to 16 carbon atoms such as a methyl, ethyl, n-propyl, isopropyl or n-butyl group;
  ii) an allyl group, a phenyl group, an arylalkyl group such as a benzyl group, a phenyl group mono- or disubstituted with substituents of the alkyl or alkoxy type of 1 to 6 carbon atoms or halogen atoms such as chlorine;
  iii) an alicyclic group such as an optionally substituted cyclohexyl group,
  iv) an aliphatic hydrocarbon group containing one or more hetero atoms such as O, N or S in its chain, in particular an acid, ester or alcohol function;

$R_2$ and $R_3$ may each, independently of each other, represent a $C_1$–$C_8$ alkyl group, a phenyl group, a phenyl group mono- or disubstituted with $C_1$–$C_4$ alkyl and/or $C_1$–$C_5$ alkoxy groups, or may be combined to form a cyclic chain of 6 to 8 carbon atoms;

$R_4$ and $R_5$ represent, independently of each other:
  i) a hydrogen atom, an amine function NR'R", where R' and R" each independently represent a hydrogen atom, an alkyl, cycloalkyl or phenyl group or a substituted derivative thereof; R' and R" may combine to form a cycloalkyl which may be substituted and may contain one or more hetero atoms;
  ii) a group R, OR, SR, COR or COOR, in which R represents a hydrogen atom, an alkyl group of 1 to 6 carbon atoms or an aryl or heteroaryl group;
  iii) a halogen atom, a $C_1$–$C_4$ monohaloalkyl group, the halogen being Cl or Br in particular, or a $C_1$–$C_4$ polyhaloalkyl group such as $CF_3$;
  iv) —$NO_2$, CN, SCN;
  v) a group

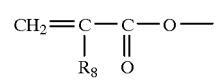

with $R_8$ representing H or $CH_3$;

vi) a group

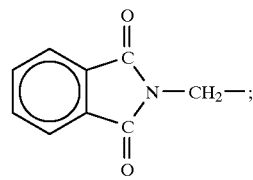

it being possible for each of the substituents $R_4$ to be present on any of the suitable carbon atoms of the indoline part of the photochromic compound, in positions 4, 5, 6 and 7, when the other is a hydrogen atom, whereas, when n=2, it is preferably for the substituents to be present in positions 4 and 5, 5 and 6, 4 and 6 or 6 and 7;

$R_6$ is chosen from groups CN,

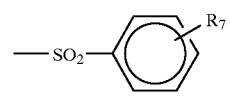

in which formula $R_7$ denotes a hydrogen atom, an alkyl having from 1 to 6 carbon atoms, an alkoxy having from 1 to 6 carbon atoms or a halogen.

Preferably, $R_7$ is in the position para to the $SO_2$ group. $R_7$ is preferably a hydrogen atom.

The preferred compounds correspond to the following formula:

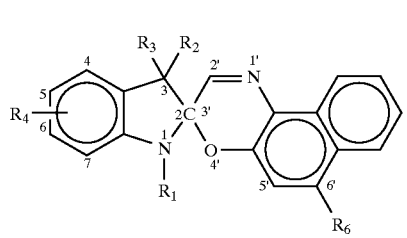
(I')

in which:
R$_1$ denotes an alkyl group having from 1 to 16 carbon atoms or an allyl group;
R$_2$ and R$_3$ represent, independently of each other, an alkyl group having from 1 to 8 carbon atoms;
R$_4$ denotes a halogen atom, a hydrogen atom or an alkoxy radical having from 1 to 6 carbon atoms, a group

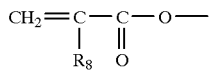

with R$_8$ denoting H or CH$_3$, or a group

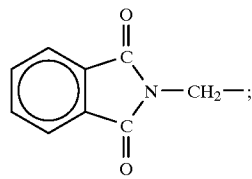

R$_6$ has the meaning mentioned above in formula (I).

In the compounds of the invention, R$_6$ is preferably a cyano group. R$_4$ is preferably in position 5 of the indoline group and denotes an alkoxy group, a halogen or a group

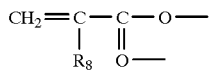

with R$_8$ denoting H or CH$_3$, and/or at least one of the groups R$_1$ and R$_2$ is an alkyl group containing at least 2 carbon atoms.

Such compounds show intense colorations when they are introduced into a matrix.

The compounds more particularly preferred correspond to the following formula:

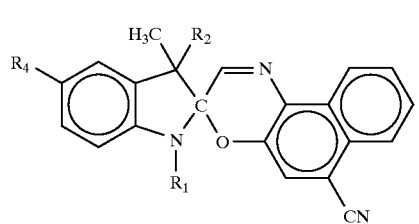
(I")

in which:
R$_1$ denotes an alkyl having from 1 to 16 carbon atoms or an allyl group;
R$_2$ denotes an alkyl having from 1 to 8 carbon atoms;
R$_4$ denotes a halogen atom, a hydrogen atom, an alkoxy radical having from 1 to 6 carbon atoms or a radical

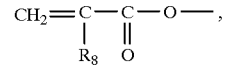

with R$_8$ denoting H or CH$_3$.

In formula (I") defined above:
R$_1$ preferably denotes a methyl, hexadecyl or allyl radical;
R$_2$ preferably denotes a methyl or ethyl radical;
R$_4$ preferably denotes a hydrogen, chlorine, a methoxy radical or the radical

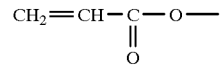

The compounds according to the invention may be obtained according to a process comprising the condensation of a Fischer base with an ortho-aminophenol substituted in position 4 with a cyano or benzylsulfonyl group, in a solvent medium such as toluene, in the presence of an oxidizing agent such as dimethyl sulfoxide.

In particular, the compounds of formula (I) according to the invention may be obtained according to this process, by condensation of a Fischer base of formula:

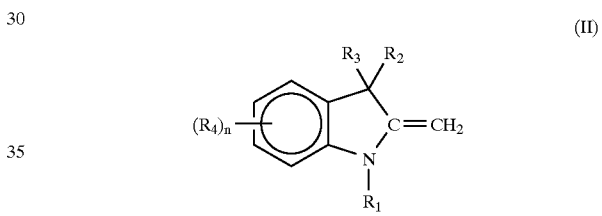
(II)

in which R$_1$, R$_2$, R$_3$, R$_4$ and n have the same meanings indicated above, with an annellated ortho-aminophenol of formula:

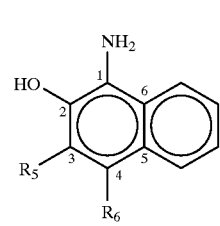
(III)

where R$_5$ and R$_6$ have the same meanings indicated above, in a solvent medium such as toluene, in the presence of an oxidizing agent such as dimethyl sulfoxide.

According to this process, a dehydrating agent such as calcium or magnesium sulfate and/or an agent for activating the oxidizing agent, such as sodium hydrogen carbonate, are also preferably used so as to promote the condensation reaction and/or to increase the yield of final product.

The reaction temperature is preferably approximately between 50 and 80° C.

This process may be represented by the following reaction scheme:

REACTION SCHEME

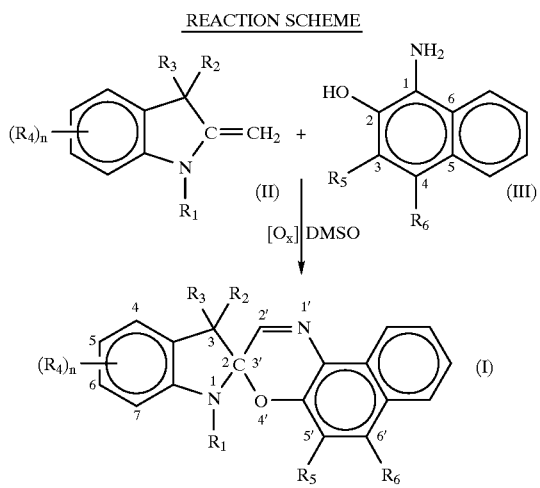

The ortho-aminophenol compounds of formula (III), substituted in position 4 with a cyano group, may be obtained by reacting a compound of formula:

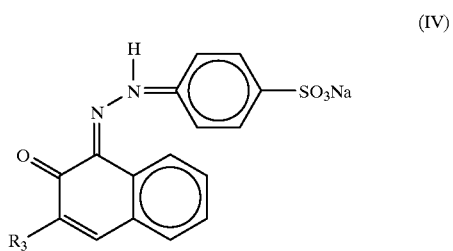

where $R_5$ has the same meaning mentioned above, with a cyanide of an alkali metal such as sodium or potassium, for a few days at 90° C., followed by filtration and saturation with carbon dioxide.

The ortho-aminophenol compounds of formula (III), in which $R_6$ is a phenylsulfonyl group, may be obtained by working according to the following scheme:

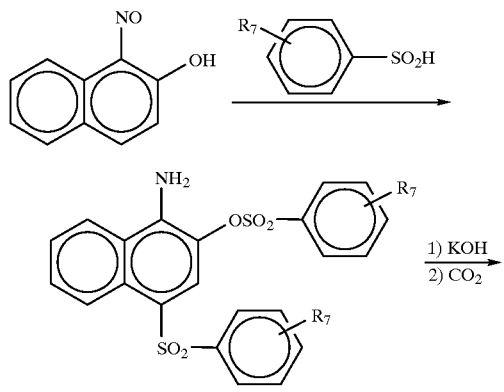

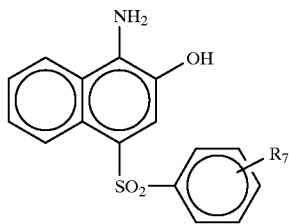

The photochromic compounds of the invention may be used to prepare photochromic ophthalmic lenses.

The compounds in accordance with the invention may be introduced into a composition intended to be applied to or to be introduced into a transparent organic polymer in order to obtain a transparent photochromic article. They may also be introduced into solid compositions such as plastic films, plates and lenses in order to produce materials which can be used, in particular, as ophthalmic lenses, sunglasses, vizors, camera optics and filters.

The liquid compositions which constitute a subject of the invention are essentially characterized in that they contain, in dissolved or dispersed form, the compounds in accordance with the invention in a medium based on solvents which are suitable to be applied or introduced into a transparent polymer.

Solvents which can be used more particularly are organic solvents chosen from benzene, toluene, chloroform, ethyl acetate, methyl ethyl ketone, acetone, ethyl alcohol, methyl alcohol, acetonitrile, tetrahydrofuran, dioxane, ethylene glycol methyl ether, dimethylformamide, dimethyl sulfoxide, methylcellosolve, morpholine and ethylene glycol.

When the compounds in accordance with the invention are dispersed, the medium may also contain water.

According to another embodiment, the compounds in accordance with the invention may be introduced and preferably dissolved into colorless or transparent solutions prepared from polymers, from copolymers or from mixtures of transparent polymers in a suitable organic solvent.

Examples of such solutions are, inter alia, solutions of nitrocellulose in acetonitrile, of polyvinyl acetate in acetone, of polyvinyl chloride in methyl ethyl ketone, of polymethylformamide, of polyvinylpyrrolidone in acetonitrile, of polystyrene in benzene or of ethylcellulose in methylene chloride.

These compositions may be applied to transparent supports such as supports made of polyethylene glycol terephthalate, borylated paper, cellulose triacetate and dried to obtain a photochromic material which can become colored in the presence of ultraviolet radiation, and which returns to the non-colored and transparent state in the absence of the source of radiation.

The photochromic compounds of the present invention, or the compositions containing them defined above, may be applied or incorporated into a solid transparent polymerized organic material which is suitable for ophthalmic components such as ophthalmic lenses or materials which are useful for use in sunglasses, vizors, camera optics and filters.

As examples of transparent solid materials which can be used to prepare ophthalmic lenses in accordance with the invention, mention may be made of polyol(allyl carbonate) polymers, polyacrylates, poly(alkyl acrylates) such as polymethyl methacrylates, cellulose acetate, cellulose triacetate, cellulose propionate acetate, cellulose butyrate acetate, poly (vinyl acetate), poly(vinyl alcohol), polyurethanes, polycarbonates, polyethylene terephthalates, polystyrenes, poly(styrenemethyl methacrylates), copolymers of styrene and of acrylonitrile, and polyvinyl butyrates.

Transparent copolymers or mixtures of transparent polymers are also suitable for producing such materials.

In this respect, mention may be made of the materials prepared from polycarbonates such as poly(4,4'-dioxyphenol-2,2-propane), polymethyl methacrylate, polyol (allyl carbonates), such as, in particular, diethylene glycol bis(allyl carbonate) and copolyers thereof such as for example, the copolymer with vinyl acetate. Mention may be made in particular of copolymers of diethylene glycol bis (allyl carbonate) and of vinyl acetate (80–90/10–20) and also the copolymer of diethylene glycol bis(allyl carbonate) with vinyl acetate, cellulose acetate and cellulose propionate, cellulose butyrate (80–85/15–20).

The polyol(allyl carbonates) are prepared using allyl carbonates of linear or branched aliphatic or aromatic liquid polyols such as aliphatic glycols of bis(allyl carbonate) or alkylene bis(allyl carbonate). Among the polyol (allyl carbonates) which may be used to prepare the solid transparent materials which can be used in accordance with the invention, mention may be made of ethylene glycol bis(allyl carbonate), diethylene glycol bis(2-methallyl carbonate), diethylene glycol bis(allyl carbonate), ethylene glycol bis (2-chloroallyl carbonate), triethylene glycol bis(allyl carbonate), 1,3-propanediol bis(allyl carbonate), propylene glycol bis(2-ethylallyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate) and isopropylene bisphenol bis(allyl carbonate). The most important product consists of diethylene glycol bis(allyl carbonate), also known under the name CR39.

The amount of photochromic compounds to be used in accordance with the invention, either in the composition or at the moment of its introduction into the solid support, is not critical and generally depends on the intensity of the color which the composition can impart to the material after exposure to radiation. In general, the more photochromic compounds are added the stronger will be the coloration under irradiation.

In accordance with the invention, an amount is used which is sufficient to impart to the material treated the property of changing color when exposed to radiation. This amount of photochromic compounds is generally between 0.001 and 20% by weight and preferably between 0.05 and 10% by weight relative to the total weight of the optical material or of the composition.

The photochromic compounds in accordance with the invention may also be introduced into a temporary transfer support (such as a varnish forming a coating on a substrate) and may then be transferred thermally into the substrate as described, in particular, in U.S. Pat. Nos. 4,286,957 or 4,880,667.

These compounds may be used with other photochromic compounds, such as photochromic compounds giving rise to colorations other than red, which are known in the state of the art.

Once applied to ophthalmic materials or introduced into such materials, the appearance of a coloration is observed after exposure to UV radiation and the return to the original color or to transparency is observed when exposure to the UV radiation is interrupted.

The compounds in accordance with the invention have the advantage of allowing this change in coloration a large number of times, and at very variable temperatures of between 0 and 40° C.

The examples which follow are intended to illustrate the invention without, however, being limiting in nature.

EXAMPLES

Example 1

6'-cyano-1,3,3-trimethylspiro[indoline-[2,3'][3H] naphth-[2,1-b][1,4]-oxazine

A—Synthesis of 4-cyano-2-hydroxynaphthylamine

This synthesis is carried out according to the reaction scheme:

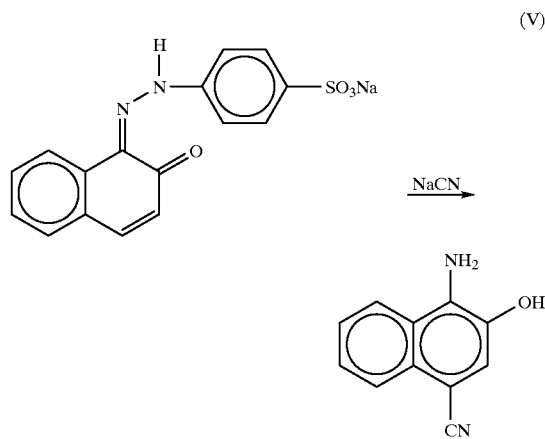

30 g (0.46 mol) of potassium cyanide are added to a solution of sodium 4-(2-hydroxy-1-naphthylazo) benzenesulfonate (10 g, 28.5 mmol) in 120 ml of water. After 2 days at 90° C., the mixture is filtered and the filtrate is saturated with carbon dioxide. The yellow precipitate is filtered off to give 2.9 g (55%) of 4-cyano-2-hydroxynaphthylamine (V).

Melting point: 206° C.

B—Synthesis of the corresponding spironaphthoxazine 10 ml of toluene are added to a mixture of 2-methylene-1,3,3-trimethylindoline (0.35 g, 2 mmol), anhydrous calcium sulfate (0.4 g), dimethyl sulfoxide (0.234 g, 3 mmol), sodium hydrogen carbonate (0.5 g) and 4-cyano-2-hydroxynaphthylamine (V) (0.405 g, 2.2 mmol) and the mixture is left stirring for 12 hours at 80° C. The mixture is filtered and washed with hot toluene (5 ml) and the filtrate is evaporated. The product is then purified by flash chromatography (90 hexane/10 ethyl acetate).

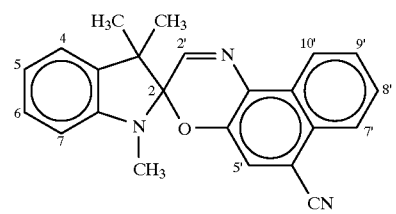

Yield: 58%

Melting point: 159° C.

$^1$H NMR (250 MHz, CDCl$_3$, TMS), δ ppm: 1.34 (3H, s, 3-CH$_3$); 1.37 (3H, s, 3-CH$_3$); 2.76 (3s, N—CH$_3$); 6.59 (1H, d, 7-H); 6.93 (1H, dd, 5-H); 7.09 (1H, d, 4-H); 7.24 (1H, dd, 6-H); 7.46 (1H, s, 5'-H); 7.59 (1H, dd, 8'-H); 7.69 (1H, dd, 9'-H); 7.89 (1H, s, 2'-H); 8.14 (1H, d, 7'-H); 8.66 (1H, d, 10'-H).

$^{13}$C NMR (62.5 MHz, CDCl$_3$, TMS), δ ppm: 20.9 (q, 3-CH$_3$); 25.6 (q, 3-CH$_3$); 29.9 (q, N—CH$_3$); 52.2 (s, 3-C); 99.0 (s, 2-C); 107.5 (d, 7-C); 120.5 (d, 5-C); 121.7 (d, 4-C); 122.7 (d, 10'-C); 123.4 (d, 5'-C); 125.3 (d, 7'-C); 126.8 (d, 8'-C); 128.4 (d, 6-C); 128.7 (d, 9'-C); 154.6 (d, 2'-C).

OPEN FORM (toluene): (shoulder: 597 nm); λ$_{max}$: 644 nm.

CLOSED FORM (acetonitrile): λ$_{max}$ nm (ε):206 (46700) 231(e) (43700); 236 (46300); 244 (51800); 294 (5000); 317 (5800); 330 (7400); 368 (7200); 386 (5400).

ε represents the molar coefficient of extinction of general formula:

ε=(log Io/I) C.l where

Io is the incident light intensity

I is the transmitted light intensity

C is the molar concentration l is the length (cm) of the solution passed through.

Example 2

6'-cyano-5-methoxy-1,3,3-trimethylspiro[indoline[2,3']-[3H]naphth[2.1-b][1.4]oxazine]

5 ml of toluene are added to the mixture of 5-methoxy-2-methylene-1,3,3-trimethylindoline (0.203 g, 1 mmol), 4-cyano-2-hydroxynaphthylamine hydrochloride (0.255 g, 1.1 mmol), triethylamine (0.152 g, 1.5 mmol), anhydrous calcium sulfate (0.2 g), dimethyl sulfoxide (0.117 g, 1.5 mmol) and sodium hydrogen carbonate (0.25 g) and the mixture is left stirring for 12 hours at 80° C. The mixture is filtered and washed with hot toluene (2 ml) and the filtrate is evaporated. The product is then purified by flash chromatography (90 hexane/10 ethyl acetate).

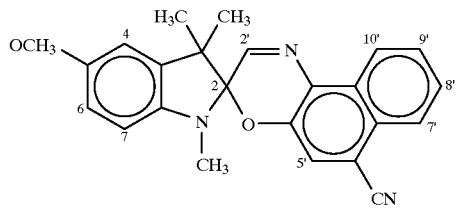

Yield: 65%

Melting point: 128° C.

$^1$H NMR (250 MHz, CDCl$_3$, TMS), δ ppm: 1.33 (3H, s, 3-CH$_3$); 1.38 (3H, s, 3-CH$_3$); 2.69 (3H, s, N—CH$_3$); 3.81 (3H, s, O—CH$_3$); 3.50 (1H, d, 7-H); 6.72–6.78 (2H, m, 4 and 6-H); 7.47 (1H, s, 5'-H); 7.59 (1H, dd, 8'-H); 7.70 (1H, dd, 9'-H); 7.88 (1H, s, 2'-H); 8.13 (1H, d, 7'-H); 8.66 (1H, d, 10'-H).

$^{13}$C NMR (62.5 MHz, CDCl$_3$, TMS), δppm: 20.7 (q, 3-CH$_3$); 25.5 (q, 3-CH$_3$); 30.1 (q, N—CH$_3$); 52.4 (s, 3-C); 56.0 (q, O—CH$_3$); 99.4 (s, 2-C); 107.7 (d, 7-C); 109.4 (d, 4 or 6-C); 112.0 (d, 4 or 6-C); 122.5 (d, 10'-C); 123.3 (d, 5'-C); 125.2 (d, 7'-C); 126.7 (d, 8'-C); 128.5 (d, 9'-C); 154.3 (d, 2'-C).

OPEN FORM (shoulder: 606 nm); λ$_{max}$ (toluene): 659 nm.

CLOSED FORM (acetonitrile): λ$_{max}$ nm (ε): 203 (62600); 231 (e) (47600); 236 (51600); 244 (56600); 316 (8800); 329 (8200); 368 (7500); 371 (7500); 388(e) (5300).

Example 3

5-chloro-6'-cyano-1,3,3-trimethylspiro[indoline[2,3']-[3H]naphth[2,1-b][1,4]oxazine]

Obtained by reaction of 4-cyano-2-hydroxynaphthylamine (V) with 5-chloro-2-methylene-1,3,3-trimethylindoline.

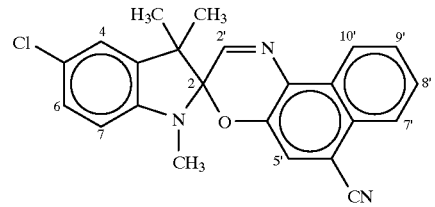

Yield: 50%

Melting point: 175° C.

$^1$H NMR (250 MHz, CDCl$_3$, TMS), δ ppm: 1.32 (3H, s, 3-CH$_3$); 1.37 (3H, s, 3-CH$_3$); 2.73 (3H, s, N—CH$_3$); 6.49 (1H, d, 7-H); 7.04 (1H, d, 4-H); 7.18 (1H, dd, 6-H); 7.46 (1H, s, 5'-H); 7.60 (1H, dd, 8'-H); 7.70 (1H, dd, 9'-H); 7.87 (1H, s, 2'-H); 8.14 (1H, d, 7'-H); 8.65 (1H, d, 10'-H). $^{13}$C NMR (62.5 MHz, CDCl$_3$, TMS), δ ppm: 20.6 (q, 3-CH$_3$); 25.2 (q, 3-CH$_3$); 29.7 (q, N—CH$_3$); 52.2 (s, 3-C); 98.9 (s, 2-C); 108.2 (d, 7-C); 122.1 (d, 4-C); 122.5 (d, 10'-C); 123.0 (d, 5'-C); 125.1 (d, 7'-C); 126.7 (d, 8'-C); 127.9 (d, 6-C); 128.5 (d, 9'-C); 153.7 (d, 2'-C).

OPEN FORM: λ$_{max}$ (toluene): 644 nm.

CLOSED FORM (acetonitrile): λ$_{max}$ nm (ε):206 (47500); 231 (47400); 235 (47300); 244 (48500); 316: (7500); 330 (8000); 367 (7900); 370(c) (7700); 384(e) (5900).

Example 4

6'-cyano-1,3-dimethyl-3-ethylspiro[indoline[2,3'] [3H]-naphth[2,1-b][1,4]oxazine]

Obtained by reaction of 4-cyano-2-hydroxynaphthylamine (V) with 1,3-dimethyl-3-ethyl-2-methyleneindoline.

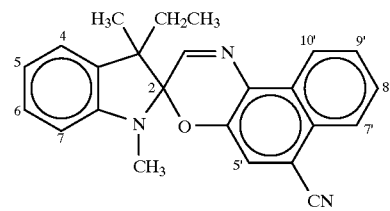

Yield: 42%

Melting point: 162° C.

$^1$H NMR (250 MHz, CDCl$_3$, TMS), δ ppm (δ ppm of the 2nd diastereoisomer): 0.83 (0.87) (3H, t, 3-CH$_2$CH$_3$); 1.40 (1.29) (3H, s, 3-CH$_3$); 1.63–2.17 (2H, m, 3-CH$_2$); 2.61 (2.75) (3H, s, N—CH$_3$); 6.53 (6.60) (1H, d, 7-H); 6.92 (6.91) (1H, dd, 5-H); 7.10 (7.08) (1H, d, 4-H); 7.22 (1H, dd, 6-H); 7.48 (7.46) (1H, s, 5'-H); 7.53–7.65 (2H, m, 8' and 9'-H); 7.91 (7.90) (1H, s, 2'-H); 8.14 (8.12) (1H, d, 7'-H); 8.69 (8.66) (1H, d, 10'-H).

OPEN FORM: λ$_{max}$ (toluene): 643 nm.

CLOSED FORM (acetonitrile): λ$_{max}$ nm (ε): 206 (47100); 230(e) (45000); 236 (48500); 244 (54200); 294

(5600); 317(e) (6400); 330 (8000); 367 (8100); 371(e) (8000); 386(e) (6200).

Example 5

1-allyl-6'-cyano-3,3-dimethylspiro[indoline][2,3'] [3H]-naphth[2,1-b][1,4]oxazine]

Obtained by reaction of 4-cyano-2-hydroxynaphthylamine (V) with 1-allyl-3,3-dimethyl-2-methyleneindoline.

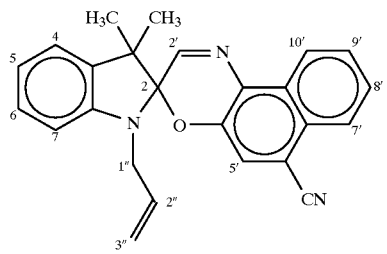

Yield: 34%

Melting point: 149° C.

$^1$H NMR (250 MHz, CDCl$_3$, TMS), δ ppm: 1.33 (3H, s, 3-CH$_3$); 1.39 (3H, s, 3-CH$_3$); 3.70–3.95 (2H, m, 1"-H); 5.05–5.30 (2H, m, 3"-H); 5.75–5.95 (1H, m, 2"-H); 6.62 (1H, d, 7-H); 6.92 (1H, dd, 5-H); 7.09 (1H, dd, 4-H); 7.20 (1H, dd, 6-H); 7.43 (1H, s, 5'-H); 7.58 (1H, dd, 8'-H); 7.68 (1H, dd, 9'-H); 7.88 (1H, s, 2'-H); 8.13 (1H, d, 7'-H); 8.64 (1H, d, 10'-H).

$^{13}$C NMR (62.5 MHz, CDCl$_3$, TMS), δ ppm: 20.8 (q, 3-CH$_3$); 25.6 (q, 3-CH$_3$); 46.9 (t, 1"); 52.7 (s, 3-C); 99.3 (s, 2-C); 107.9 (d, 7-C); 116.7 (t, 3"-C); 120.2 (d, 5-C); 121.5 (d, 4-C); 122.5 (d, 10'-C); 123.2 (d, 5'-C); 125.1 (d, 7'-C); 126.6 (d, 8'-C); 128.1 (d, 6-C); 128.4 (d, 9'-C); 133.9 (d, 2'-C).

OPEN FORM: $\lambda_{max}$ (toluene): 645 nm.

CLOSED FORM (acetonitrile): $\lambda_{max}$ (ε) : 205 (46000); 236 (48000); 245 (53300); 318 (5900); 331 (7500); 368 (7700); 371 (7700); 385(e) (6200).

Example 6

6'-cyano-3,3-dimethyl-1-hexadecylspiro[indoline[2,3']-[3H]naphth[2,1-b][1,4]oxazine]

Obtained by reaction of 4-cyano-2-hydroxynaphthylamine with 3,3-dimethyl-1-hexadecyl-2-methyleneindoline.

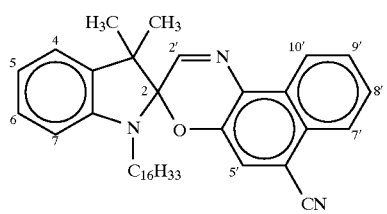

Oil

Yield: 54%.

$^1$H NMR (250 MHz, CDCl$_3$, TMS), δ ppm: 1.08–1.12 (m, C$_{15}$H$_{31}$); 1.19 (3H, s, 3-CH$_3$); 1.23 (3H, s, 3-CH$_3$); 3.02 (2H, t, N—CH$_2$); 6.58 (1H, d, 7-H); 6.95 (1H, dd, 5-H); 7.09 (1H, d, 4-H); 7.25 (1H, ddd, 6-H); 7.47 (1H, s, 5'-H); 7.59 (1H, dd, 8'-H); 7.70 (1H, dd, 9'-H); 7.88 (1H, s, 2'-H); 8.14 (1H, d, 7'-H); 8.68 (1H, d, 10'-H).

OPEN FORM: $\lambda_{max}$ (toluene): 647 nm.

Example 7 (comparative)

Compound 1,3,3-trimethylspiro[indoline[2,3'][3H] naphth-[2,1-b][1,4]oxazine]

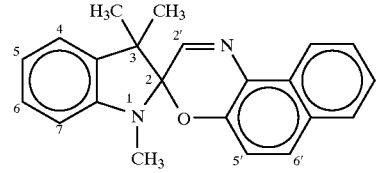

I. Photochromic Properties in Solution of the Compounds of Examples 1 to 7

Spectrokinetic Parameters (measured in toluene at 25° C. at a concentration of $2.5 \times 10^{-5}$ M)

| EXAMPLE | $\lambda_{max}$ (nm) | Kinetic constant of thermal decoloration $k_\Delta$ in s$^{-1}$ | $A_0$ Colorability |
|---|---|---|---|
| 1 | 644 | 0.22 | 1.03 |
| 2 | 659 | 0.20 | 0.9 |
| 3 | 644 | 0.32 | 1.05 |
| 4 | 643 | 0.14 | 0.86 |
| 5 | 645 | 0.33 | 1.06 |
| 6 | 647 | 0.33 | |
| 7 (comparative) | 590 | | |

The spectrokinetic parameters are determined as follows.

Toluene solutions each containing one of the compounds of Examples 1 to 7 are irradiated with UV radiation.

The measurements are taken at 25° C. (±0.2° C. controlled by external thermostat of the Hubert-ministat type) in a cylindrical quartz cell 10 mm in cross section and with an optical path length of 10 cm.

Recording of the absorption spectrum in the visible region using a rapid spectrometer of the Warner-Swasey type makes it possible to determine $\lambda_{max}$ (wavelength at the absorption maximum) and $A_0$ (initial absorbance or optical density at $\lambda_{max}$) measured immediately after the flash of coloration. The decrease in $A_0$ as a function of time allows the kinetic constant of thermal decoloration $k_{66}$ to be calculated.

For this, the samples are photolyzed by discharge tubes powered by a bank of capacitors:

energy of the flashes: about 60 J duration of the flashes: 50 μs.

It is observed that the values of $\lambda_{max}$ for the compounds according to the invention are markedly higher than for compound 7 of the prior art taken as a reference and then for the compounds of application JP 3,251,587.

II. Comparative Study Between a Compound of the Invention and a Homolog of the Prior Art Not Substituted in the 6' Position 1. Study of the photochromic kinetics and of the absorption spectrum in the visible region of the open form, in a polymer matrix.

The photochromic compound A of Example 1, of formula:

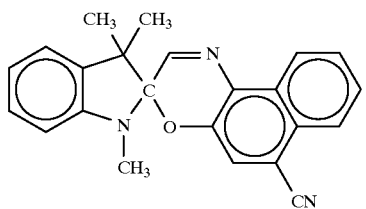

(A)

is compared with compound B of the prior art which is not substituted in the 6' position, of formula:

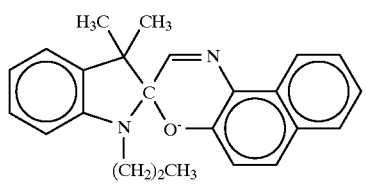

(B)

These compounds are incorporated into a thermosetting polyurethane varnish in a proportion of 5% by weight and are applied to a glass made of diethylene glycol bis(allyl carbonate)polymer (Orma® glass).

The photochromic coating is about 15 μm in thickness.

The photochromic coatings are irradiated by a 150 W xenon lamp, 0.5 mW/cm$^2$, 13 Klux for 15 minutes (phase of coloration of photochromic varnish). The irradiation is then stopped. A decoloration phase occurs.

The variation in the percentage of transmission of the photochromic varnish as a function of time is measured during the two phases by emplacement at the wavelength $\lambda_{max}$ corresponding to the absorption maximum of each compound.

The absorption spectrum in the visible region of the open form of each compound incorporated into the varnish is also recorded.

The kinetic study of compound A was performed at 35° C. at the wavelength corresponding to the absorption maximum $\lambda_{max}$=650 nm.

BRIEF DESCRIPTION OF THE DRAWINGS

The results are given in Table 1 and in FIG. 1.

The absorption spectra in the visible region for the photochromic varnish containing compound A were run at 20 and 35° C. and are represented in FIGS. 3 and 4.

The kinetic study of compound B was carried out at 20 and 35° C. with $\lambda_{max}$=610 nm.

Figure 2:
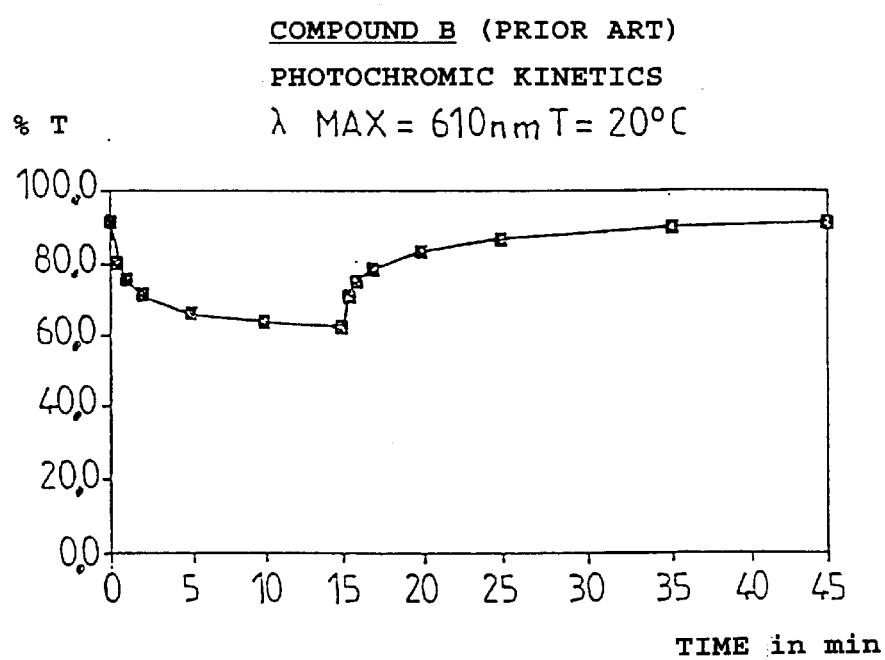

The results at 20° C. are given in Table 2 and FIG. 2.

Figure 5:
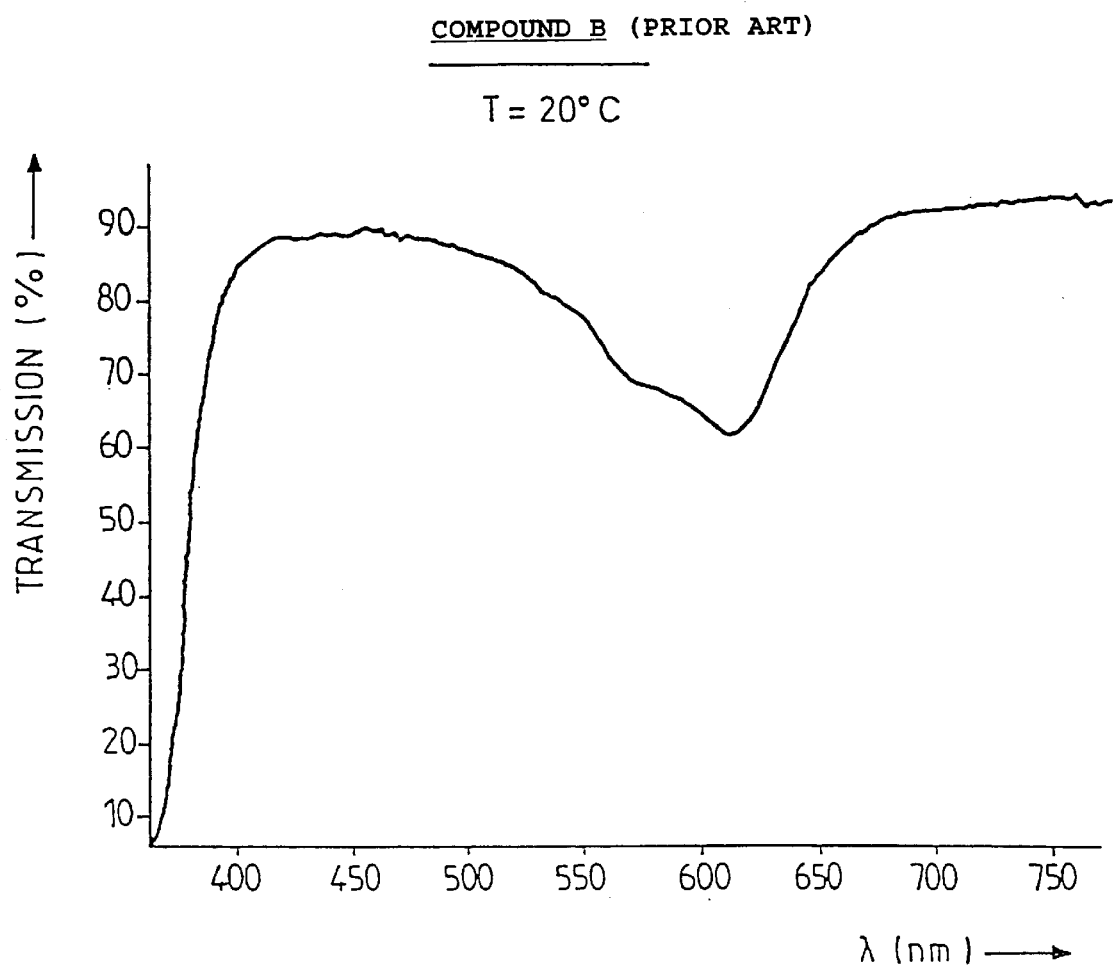

The absorption spectrum in the visible region of the varnish containing compound B was carried out at 20° C. and is represented in FIG. 5.

Results

α. PHOTOCHROMIC KINETICS OF COMPOUND A AT 35° C. AND $\lambda_{max}$=650 nm.

TABLE 1

| Time in min | Time in sec | % transmission | O.D. |
|---|---|---|---|
| 0 | 0 | 92.1 | 0.036 |
| 0.5 | 30 | 51.4 | 0.289 |
| 1 | 60 | 41.1 | 0.386 |
| 2 | 120 | 31.4 | 0.503 |
| 5 | 300 | 18.3 | 0.738 |
| 10 | 600 | 11.5 | 0.939 |
| 15 | 900 | 10 | 1.000 |
| 15.5 | 930 | 27.8 | 0.556 |
| 16 | 960 | 34.8 | 0.458 |
| 17 | 1020 | 56.7 | 0.246 |
| 20 | 1200 | 83.5 | 0.078 |
| 25 | 1500 | 90 | 0.046 |
| 35 | 2100 | 91.1 | 0.040 |

β. PHOTOCHROMIC KINETICS OF COMPOUND B AT 20° C. AND $\lambda_{max}$=610 nm.

TABLE 2

| Time in min | Time in sec | % transmission | O.D. |
|---|---|---|---|
| 0 | 0 | 91.6 | 0.038 |
| 0.5 | 30 | 79.9 | 0.097 |
| 1 | 60 | 75.6 | 0.121 |
| 2 | 120 | 71.2 | 0.148 |
| 5 | 300 | 65.5 | 0.184 |
| 10 | 600 | 63 | 0.201 |
| 15 | 900 | 61.4 | 0.212 |
| 15.5 | 930 | 70.2 | 0.154 |
| 16 | 960 | 74 | 0.131 |
| 17 | 1020 | 77.6 | 0.110 |
| 20 | 1200 | 82.3 | 0.085 |
| 25 | 1500 | 85.5 | 0.068 |
| 35 | 2100 | 88.2 | 0.055 |
| 45 | 2700 | 89.3 | 0.049 |

γ. PHOTOCHROMIC KINETICS OF COMPOUND B AT 35° C. AND $\lambda_{max}$=610 nm.

After irradiation for 15 minutes, a percentage of transmission of 85–86% is observed, whereas in the initial, non-excited state, the transmission is 90%. The photochromic performances of compound B are very poor at 35° C.

INTERPRETATION OF THE RESULTS

The absorption spectrum in the visible region for compound B at 20° C., represented in FIG. 5, shows that the colorability of compound B is very poor.

Figure 1:
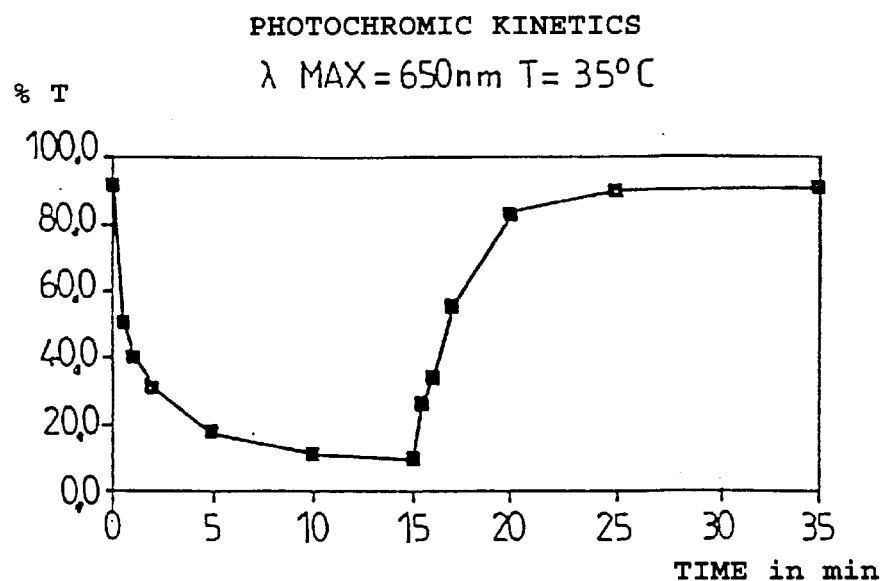

The results of Tables 1 and 2 and of FIGS. 1 and 2 relating to the study of the photochromic kinetics of compounds A and B, after UV irradiation for 15 minutes, are that:

compound B of the prior art, in open form, leads, at 20° C., to a coloration of low intensity (optical density: O.D.=0.212);

whereas compound A very rapidly achieves, at a temperature of 35° C., a coloration 5 times as intense (O.D.=1.00).

Figure 3:
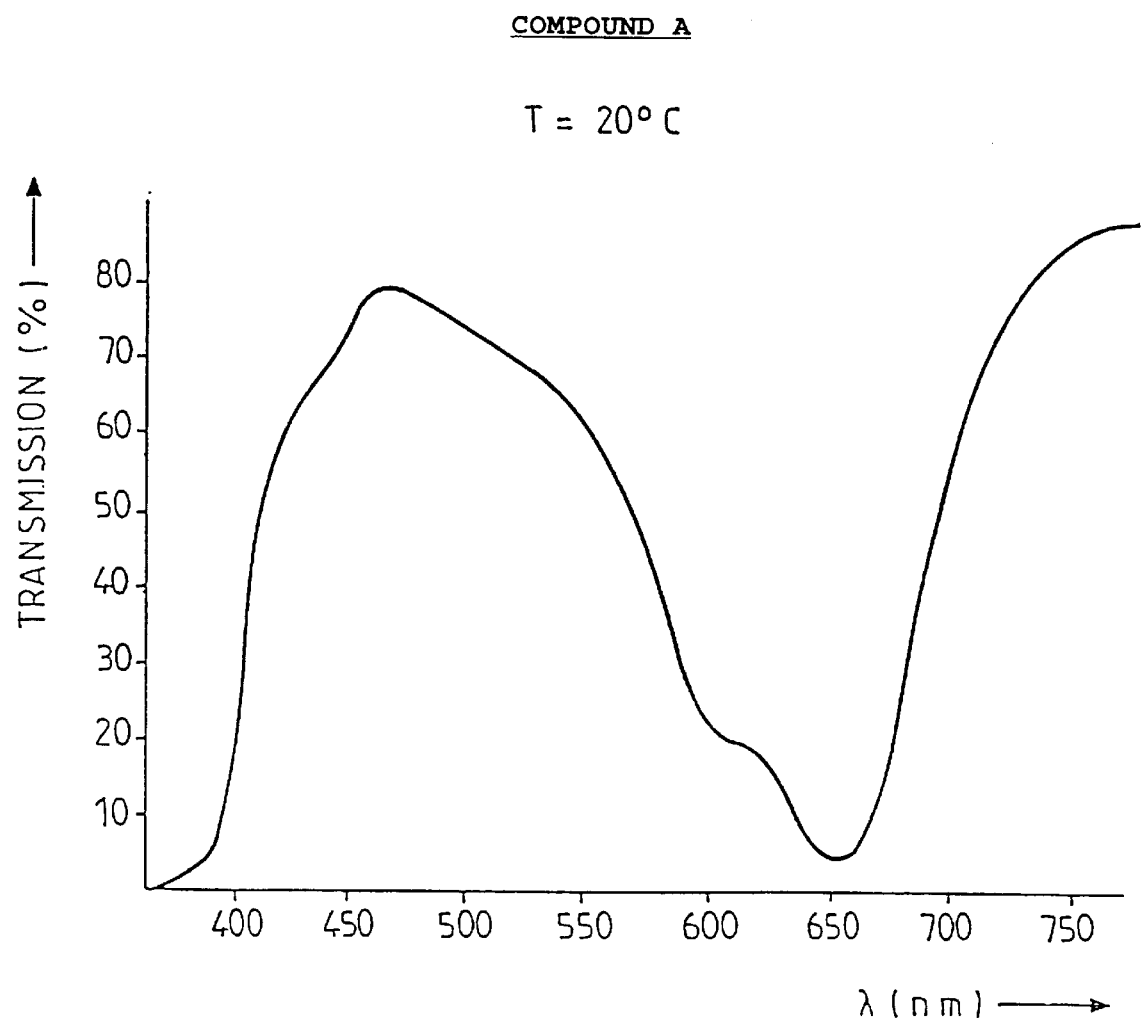
Figure 4:
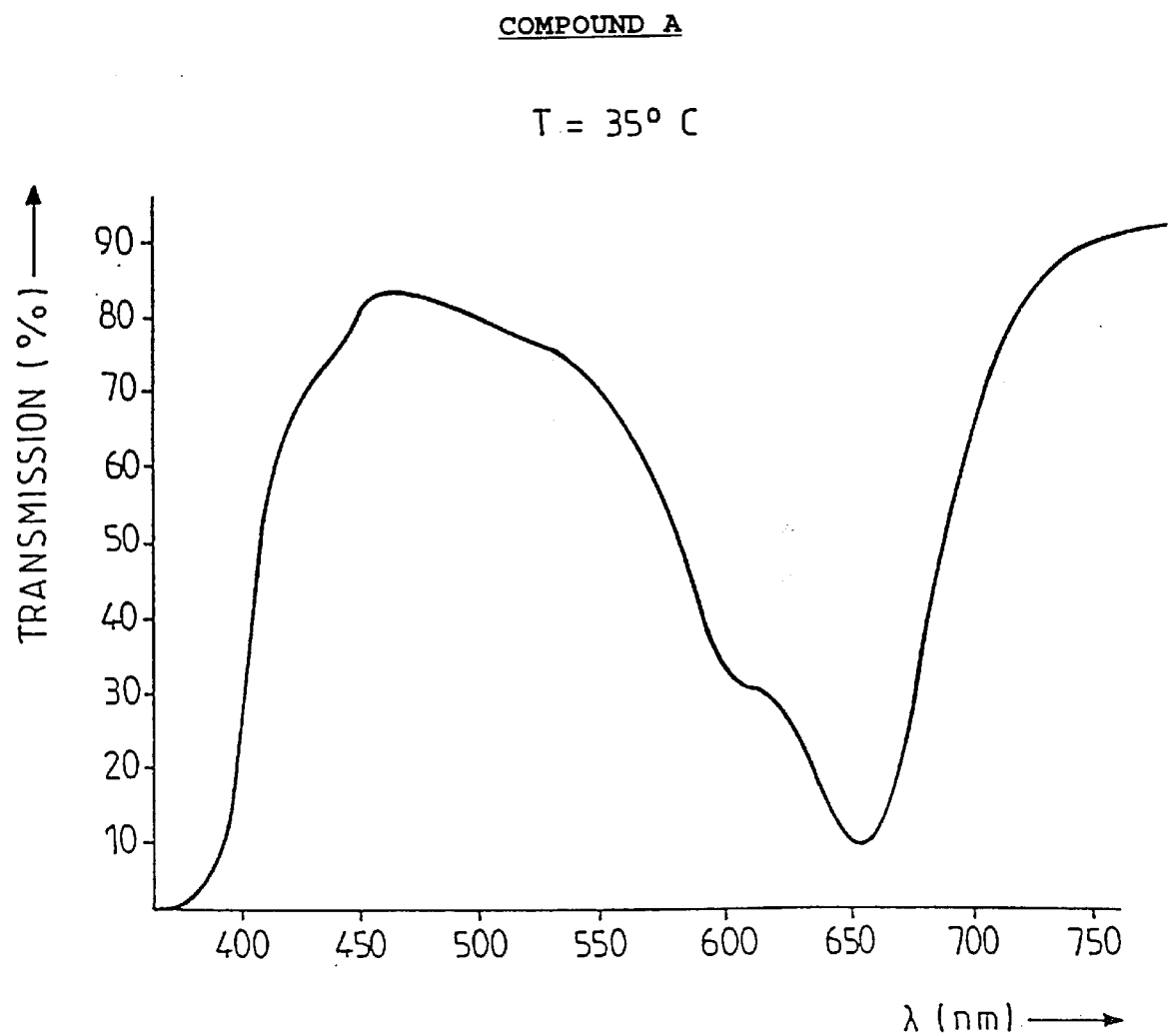

FIGS. 3, 4 and 5 relating to the absorption spectra in the visible region for compounds A and B after irradiation for 15 minutes confirm the fact that compound A, in the open form, has a colorability of higher amplitude than compound B, at 20° C.

They also show that at 35° C., compound A has a strong coloration at the absorption maximum ($\lambda_{max}$).

2. Study of the UV absorption spectra of the closed form

The photochromic compound A of Example 1 is compared with the homologous compound C, which is not substituted in the 6' position, of formula:

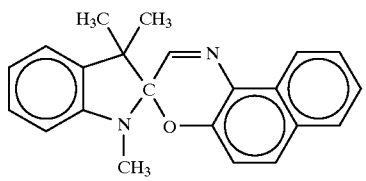

(C)

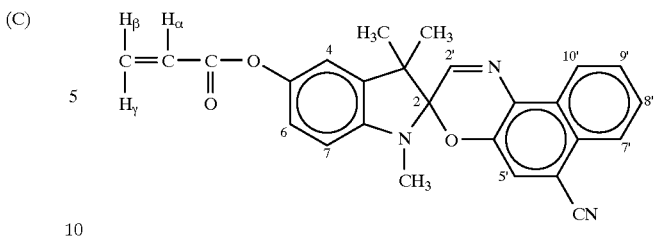

Figure 6:
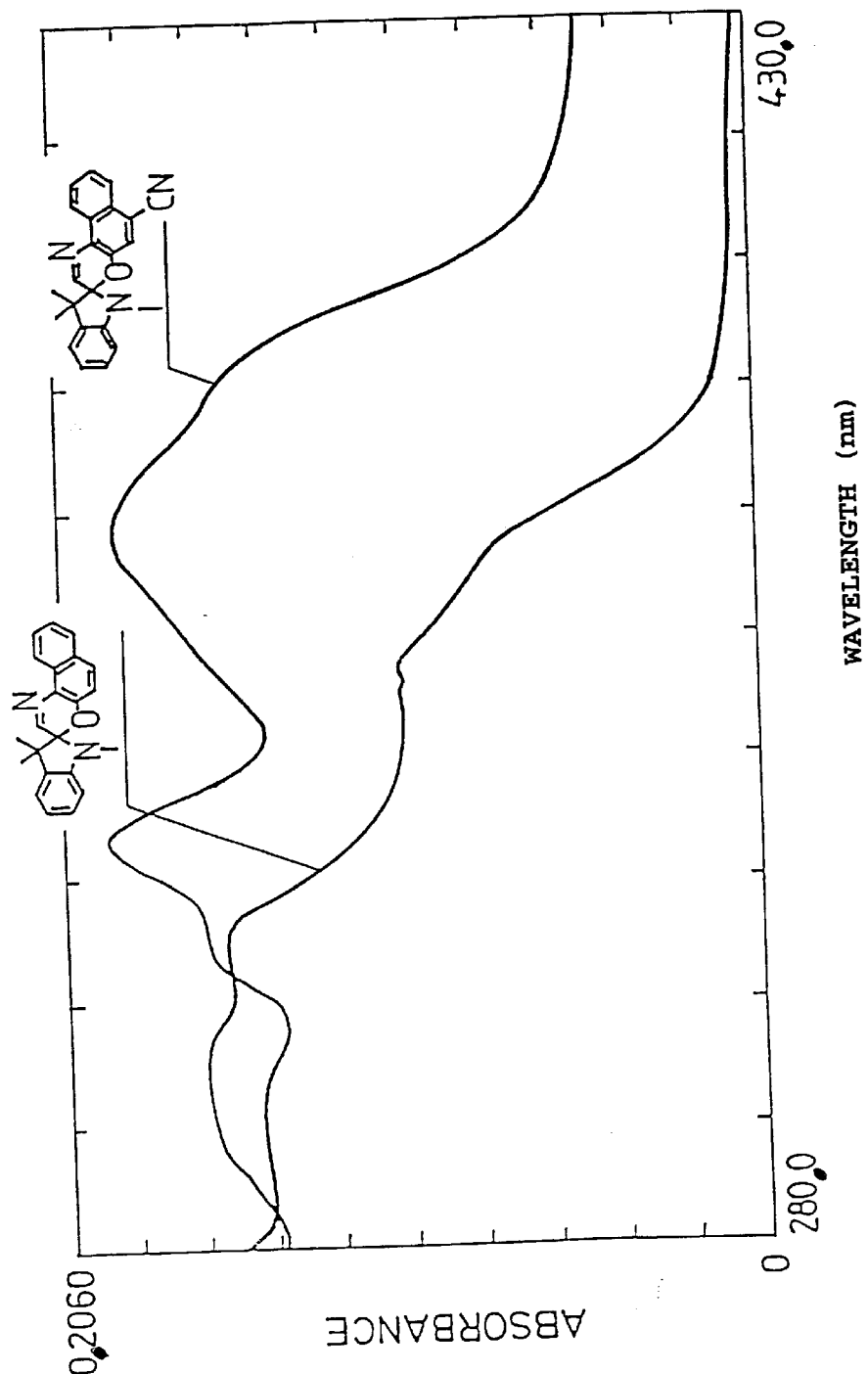

The absorption spectra of the closed form are measured for compounds A and C in solution in acetonitrile. A comparison of the two spectra is shown in FIG. 6.

The result from this figure is that compound A shows a UV absorption spectrum of the closed (non-excited) form, a shift of the absorption bands towards longer wavelengths and of the absorption maxima for the long wavelengths are observed, the amplitude of which is substantially larger when compared with the bands of the UV absorption spectrum for compound B in its closed form.

Example 8

5-acryloxy-6'-cyano-1,3,3-trimethylspiro[indoline-2, 3'-[3H]naphth[2,1-b][1,4]oxazine]

Step 1

6'-cyano-5-hydroxy-1,3,3-trimethylspiro[indoline-2, 3'-[3H]naphth[2,1-b][1,4]-oxazine]

Obtained by reaction of 4-cyano-2-hydroxynaphthylamine (V) with 5-hydroxy-2-methylene-1, 3,3-trimethylindolenine.

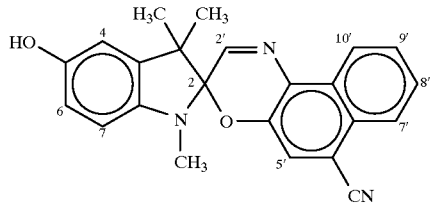

Yield: 30%

Melting point: 205–206° C.

$^1$H NMR (250 MHz, acetone-d6, TMS), δ ppm: 1.31 (3H, s, 3-CH$_3$); 1.37 (3H, s, 3-CH$_3$); 2.69 (3H, s, N—CH$_3$); 6.49 (1H, d, 7-H); 6.68 (1H, dd, 6-H); 6.71 (1H, d, 4-H); 7.65–7.79 (3H, m, 5',8' and 9'-H); 7.82 (1H, s, 2'-H); 8.01 (1H, s, OH); 8.09 (1H, d, 7'-H); 8.69 (1H, d, 10'-H).

Step 2

0.15 g of acryloyl chloride is added dropwise to the cooled (0° C.) solution of 0.1 g of SPO obtained in the above step and 0.3 g of triethylamine in 50 ml of CH$_2$Cl$_2$.

The mixture is left stirring for 2 hours at room temperature. Evaporation of the solvent and purification by flash chromatography (85 hexane/15 ethyl acetate) gives the desired product.

Yield: 79%

Melting point: 135–136° C.

$^1$H NMR (250 MHz, CDCl$_3$ [sic], TMS), δ ppm: 1.32 (3H, s, 3-CH$_3$); 1.39 (3H, s, 3-CH$_3$); 2.74 (3H, s, N—CH$_3$); 6.01 (1H, d, Hβ); 6.33 (1H, dd, Hα); 6.51 (1H, d, 7-H); 6.61 (1H, d, Hγ); 6.87 (1H, d, 4-H)); 6.98 (1H, s, 5'-H); 7.61 (1H, dd, 8'-H); 7.70 (1H, dd, 9'-H); 7.88 (1H, s, 2'-H); 8.14 (1H, d, 7'-H); 8.66 (1H, d, 10'-H).

Open form: $\lambda_{max}$ (toluene): 646 nm

Example 9

6'-p-tolylsulfonyl-1,3,3-trimethylspiro[indoline-2,3'-[3H] naphth[2.1-b][1,4]oxazine]

A. Synthesis of 4-p-tolylsulfonyl-2-hydroxynaphthylamine

This synthesis is carried out according to the following reaction scheme:

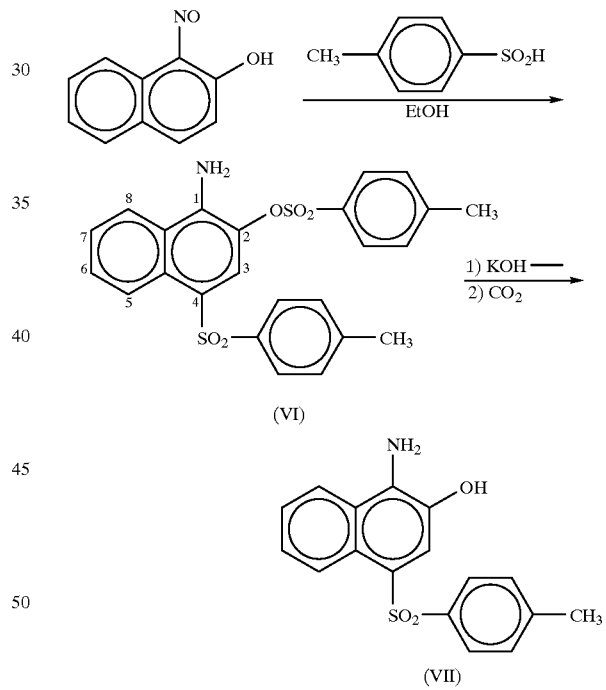

10 g (0.058 mol) of 1-nitroso-2-naphthol are added to a cooled solution of p-toluenesulfinic acid (27 g, 0.173 mol) in 50 ml of ethanol. The mixture is heated at reflux for 1 hour and cooled and the product is left to precipitate under cold conditions for 12 hours. After filtration and two crystallizations from ethanol, 9.2 g (34%) of compound (VI) are obtained in the form of white crystals.

Melting point: 151–152° C.

$^1$H NMR (250 MHz, CDCl3 [sic], TMS), δ ppm: 2.34 (3H, s, CH$_3$); 2.49 (3H, s, CH$_3$); 5.06 (2H, broad s, NH$_2$); 7.20–7.86 (12H, m, arom. H); 8.5 (1H, d, 8-H).

A solution of 3.4 g (7.25 mmol) of tosylate (VI) in 20 ml of ethanol is mixed with a solution of 3.4 g (60.7 mmol) of potassium hydroxide in 40 ml of water. The mixture is maintained at reflux for 30 minutes, cooled, left overnight under cold conditions and filtered. The filtrate is saturated with carbon dioxide and the precipitate is filtered off and dried.

1.4 g (62%) of 4-p-tolylsulfonyl-2-hydroxynaphthylamine (VII) are obtained, which product is used in the synthesis of SPO without further purification.

Melting point: 181–184° C.

B. Synthesis of the corresponding spironaphthoxazine

The spirooxazine is obtained by reaction of 4-p-tolylsulfonyl-2-hydroxynaphthylamine (VII) with 2-methylene-1,3,3-trimethylindolenine. The reaction conditions and the purification are identical to those of Example 1.

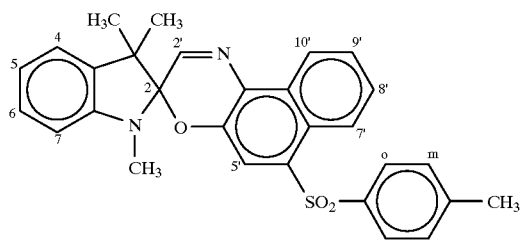

Yield: 10%

Melting point: 204–205° C.

$^1$H NMR (250 MHz, CDCl$_3$ [sic], TMS), δ ppm: 1.34 (3H, s, 3-CH$_3$); 1.35 (3H, s, 3-CH$_3$); 2.39 (3H, s, p-CH$_3$); 2.73 (3H, s, N—CH$_3$); 6.58 (1H, d, 7-H); 6.91 (1H, dd, 5-H); 7.08 (1H, d, 4-H) 7.23 (3H, m,m-H, 6-H); 7.46 (1H, dd, 8'-H); 7.58 (1H, dd, 9'-H); 7.82 (2H, d, o-H); 7.87 (1H, s, 2'-H); 8.02 (1H, s, 5'-H); 8.57 (1H, d, 7'-H); 8.66 (1H, d, 10'-H).

Open form: λ$_{max}$ (toluene): 632 nm

Example 10

6'-Phenylsulfonyl-1,3,3-trimethylspiro[indoline-2.3[3H]-naphth[2,1-b][1,4]oxazine]

A. Synthesis of 4-phenylsulfonyl-2-hydroxynaphthylamine

4-Phenylsulfonyl-2-hydroxynaphthylamine (VIII) is obtained according to the method described to produce (VII) (Example 9) from 1-nitroso-2-naphthol and benzenesulfinic acid.

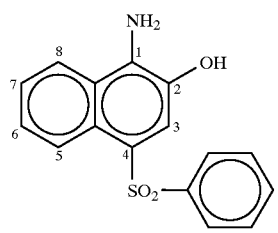
(VIII)

Yield: 16%

Melting point: 176–177° C.

B. Synthesis of the corresponding spironaphthoxazine

This is obtained by reaction of 4-phenylsulfo-2-hydroxynaphthylamine with 2-methylene-1,3,3-trimethylindolenine.

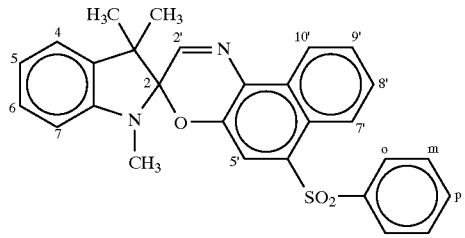

Yield: 21%

Melting point: 195–196° C.

$^1$H NMR (250 MHz, CDCl$_3$ [sic], TMS), δ ppm: 1.36 (3H, s, 3-CH$_3$); 1.37 (3H, s, 3-CH$_3$); 2.75 (3H, s, N—CH$_3$); 6.59 (1H, d, 7-H); 6.93 (1H, dd, 5H); 7.10 (1H, d, 4-H); 7.24 (1H, dd, 6-H), 7.43–7.53 (4H, m, 8'-H, p-H,m-H); 7.60 (1H, dd, 9'-H); 7.89 (1H, s, 2'-H); 7.94 (2H, d, o-H); 8.08 (1H,s, 5'-H); 8.54 (1H, d, 7'-H); 8.66 (1H, d, 10'-H)

$^{13}$C NMR (62.5 MHz, CDCl$_3$ [sic], TMS), δ ppm: 21.0 (q, 3-CH$_3$); 25.5 (q, 3-CH$_3$); 29.8 (q, N—CH$_3$); 52.2 (s, 3-C); 99.1 (s, 2-C); 107.4 (d, 7-C); 120.4 (d, 5-C); 121.2 (d, 5'-C); 121.6 (d, 4-C); 122.8 (d, 10'-C); 124.4 (d, 7'-C); 126.4 (d, 8'-C); 127.6 (d, o-C); 127.9 (d, 9'-C); 128.3 (d, 6-C); 129.3 (d, m-C); 133.4 (d, p-C); 154.6 (d, 2'-C).

Open form: λ$_{max}$ (toluene): 642 nm

Example 11

5-methoxy-6'-phenylsulfonyl-1,3,3-trimethylspiro-[indoline-2,3'[3H]naphth[2,1-b][1,4]oxazine]

This is obtained by reaction of 4-phenylsulfo-2-hydroxynaphthylamine with 5-methoxy-2-methylene-1,3,3-trimethylindolenine.

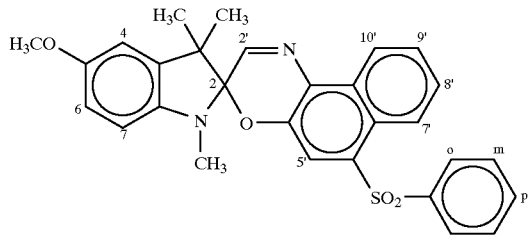

Yield: 14%

Melting point: 161–162° C.

$^1$H NMR (250 MHz, CDCl$_3$, TMS), δ ppm: 1.34 (3H, s, 3-CH$_3$); 1.38 (3H, s, 3-CH$_3$); 2.69 (3H, s, N—CH); 3.81 (3H, s, O—CH$_3$); 6.50 (1H, d, 7H); 6.74–6.77 (2H, m, 6-H, 4-H); 7.35–7.51 (4H, m, 8'-H, p-H, m-H); 7.55 (1H, dd, 9'H); 7.88 (1H, s, 2'-H); 7.93 (2H, dd, o-H); 8.10 (1H, s, 5'-H); 8.53 (1H, d, 7'-H); 8.53 (1H, d, 7'-H); 8.66 (1H, s, 10'-H).

Open form: λ$_{max}$ (toluene): 657 nm

Example 12

5-acryloxy-6'-phenylsulfonyl-1,3,3-trimethylspiro-[indoline-2,3'[3H]naphth[2,1-b][1,4]oxazine]

Step 1

5-hydroxy-6'-phenylsulfonyl-1,3,3-trimethylspiro-[indoline-2,3'[3H]naphth[2,1-b][1,4]oxazine]

Obtained by reaction of 4-phenylsulfo-2-hydroxynaphthylamine with 5-hydroxy-2-methylene-1,3,3-trimethylindolenine

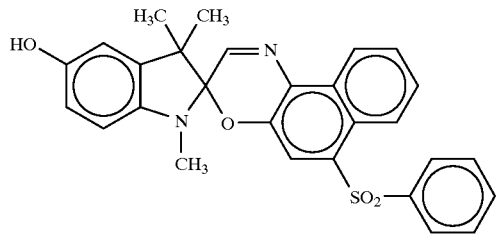

Yield: 28%

Step 2

0.1 g of SPO obtained in the above step is treated with 0.15 g of acryloyl chloride, as in Example 8, step 2. Purification by flash chromatography (85 hexane/15 ethyl acetate) gives the desired product.

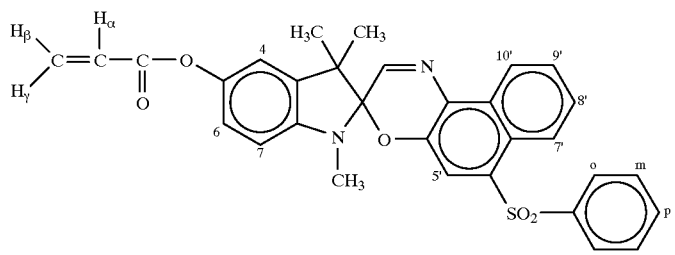

Yield: 68%

Melting point: 183–184° C.

$^1$H NMR (250 MHz, CDCl$_3$, TMS), δ ppm; 1.34 (3H, s, 3-CH$_3$); 1.39 (3H, s, 3-CH$_3$); 2.74 (3H, s, N—CH$_3$); 6.01 (1H, d, Hβ); 6.33 (1H, dd, Hα); 6.56 (1H, d, 7H); 6.61 (1H, d, Hγ); 6.89 (1H, d, 4-H); 6.97 (1H, dd, 6-H); 7.45–7.64 (5H, m, 8'-H, 9'-H, p-H, m-H); 7.88 (1H, s, 2'-H); 7.96 (2H, d, o-H); 8.07 (1H, s, 5'-H); 8.56 (2H, d, 7'-H); 8.66 (1H, d, 10'-H)

Open form: $\lambda_{max}$ (toluene): 643 nm

Example 13

Following the general synthetic scheme, the following compound is synthesized

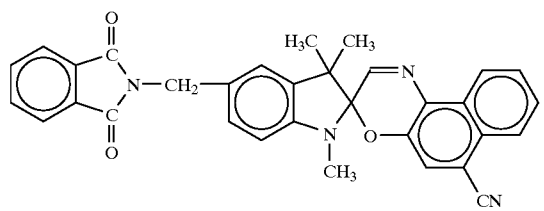

This compound may be synthesized by the reaction scheme mentioned above, using the Fischer base 1,3,3-trimethyl-2-methylene-5-N-phthalimidomethylindoline. This Fischer base and the preparation process are described in Australian Journal Chemistry 1977, Vol. 30 pp 689–694.

Spectrokinetic properties of the compounds of Examples 8 to 12

The spectrokinetic properties are measured in solution in toluene, under the same conditions as for Examples 1 to 7.

| EXAMPLE | $\lambda_{max}$ (nm) | Kinetic constant of thermal decoloration $k_\Delta$ in s−1 | $A_0$ Colorability |
|---|---|---|---|
| 8 | 646 | 0.17 | 0.77 |
| 9 | 632 | 0.15 | 1.32 |
| 10 | 642 | 0.13 | 1.17 |
| 11 | 657 | 0.20 | |
| 12 | 643 | 0.18 | 0.95 |

It is observed that the $\lambda_{max}$ values of compounds 8 to 12 are high.

Examples of use of the photochromic compounds of the invention

1) Photochromic hydrophilic soft contact lenses

Hydrophilic contact lenses made of MMA (methyl methacrylate) and NVP (N-vinylpyrrolidone) in proportions of 72.8% and 26.1%, crosslinked with 0.23% allyl methacrylate, are prepared.

The lens is obtained by mixing the N-vinylpyrrolidone with the MMA, a thermal initiator AIBN (azobisisobutyronitrile) (0.89%), 0.1 mol % of the photochromic compound, and the crosslinking agent, and the composition obtained is then polymerized thermally for 33 hours, the temperature starting at 40° C. and reaching 120° C. at the end of the cycle.

Each of the photochromic compounds of Examples 1, 2, 3, 4, 6, 8, 9, 12 and 13 is incorporated separately into MMA/NVP hydrophilic contact lenses in accordance with the above procedure.

When exposed to sunlight, the initially colorless lenses take on a green-blue coloration, which disappears when the irradiation ceases.

It is noted that the coloration appears more intense in the case of lenses incorporating the photochromic compounds of Examples 3, 4 and 8.

2) Photochromic hard contact lenses

Hard contact lenses made of PMMA (polymethyl methacrylate) are prepared by polymerization of a mixture containing 100 parts by weight of methyl methacrylate (MMA), 2 parts by weight of EGDM (ethylene glycol dimethacrylate) and 0.03 parts by weight of AIBN.

The photochromic compound of Example 8 is incorporated into the polymerizable mixture in a proportion of 0.1 mol %.

The mixture is introduced into a polypropylene tube and the polymerization is then carried out thermally by heating for 15 hours at 64° C. and then for 8 hours at 83° C.

After removal from the mould, the contact lenses are trimmed and machined.

When exposed to sunlight, the initially colorless lenses take on a green-blue coloration.

The photochromism of these lenses is particularly persistent over time.

We claim:

1. Photochromic compounds of spiro[indoline[2,3']-naphthoxazine structure, characterized in that they contain, in the 6' position, a group $R_6$ chosen from the following groups: cyano and phenylsulfonyl linked via the sulfur atom to carbon 6'.

2. Photochromic compounds according to claim 1, characterized in that they correspond to the following formula:

(I)

*[chemical structure showing spiro[indoline-naphthoxazine] with substituents $R_1, R_2, R_3, (R_4)_n, R_5, R_6$ and numbered positions]* in which:

n ranges from 0 to 4;

$R_1$ represents:

i) an alkyl group of 1 to 16 carbon atoms;

ii) an allyl group, a phenyl group, an arylalkyl group mono- or disubstituted with $C_1$–$C_6$ alkoxy groups or halogen atoms;

iii) an optionally substituted alicyclic group;

iv) an aliphatic hydrocarbon group containing one or more hetero atoms selected from O, N and S in its chain, and optionally an acid, ester or alcohol groups;

$R_2$ and $R_3$ may, independently of each other, represent a $C_1$–$C_8$ alkyl group, a phenyl group, a phenyl group mono- or disubstituted with $C_1$–$C_4$ alkyl and/or $C_1$–$C_5$ alkoxy groups, or may be combined to form a cyclic chain of 6 to 8 carbon atoms;

$R_4$ and $R_5$ represent, independently of each other:

i) a hydrogen atom, an amine function NR'R", where R' and R" each independently represent a hydrogen atom, an alkyl, cycloalkyl or phenyl group which may be substituted; R' and R" may combine to form a cycloalkyl which may be substituted and may contain one or more hetero atoms;

ii) a group R, OR, SR, COR or COOR, in which R represents a hydrogen atom, an alkyl group of 1 to 6 carbon atoms or an aryl or heteroaryl group;

iii) a halogen atom, a $C_1$–$C_4$ monohaloalkyl group, or a $C_{1-4}$ polyhaloalkyl group;

iv) —$NO_2$, —CN, —SCN, it being possible for each of the substituents $R_4$ to be present on any of the suitable carbon atoms of the indoline part of the photochromic compound, in positions 4, 5, 6 and 7, v) a group $$CH_2=C(R_8)-C(=O)-O-$$

with $R_8$ representing H or $CH_3$; or vi) a group

*[chemical structure of phthalimide-CH$_2$— group]*

$R_6$ is chosen from groups:

—CN and —$SO_2$—*[phenyl-$R_7$]* in which formula $R_7$ denotes a hydrogen atom, an alkyl having from 1 to 6 carbon atoms, an alkoxy having from 1 to 6 carbon atoms or a halogen atom.

3. Photochromic compounds according to claim 1, characterized in that they possess a spiro[indoline-2,3'[3H]napth[2,1-b][1,4]oxazine].

4. Compounds according to 2, characterized in that they correspond to the following formula:

(I')

*[chemical structure similar to (I) with $R_1, R_2, R_3, R_4, R_6$ substituents]* in which $R_1$ denotes an alkyl group having from 1 to 16 carbon atoms or an allyl group;

$R_2$ and $R_3$ represent, independently of each other, an alkyl group having from 1 to 8 carbon atoms;

$R_4$ denotes a halogen atom, a hydrogen atom, an alkoxy radical or a group $$CH_2=C(R_8)-C(=O)-O-$$

in which $R_8$ represents H or $CH_3$: and $R_6$ has the same meaning as in claim 3.

5. Compounds according to claim 4, characterized in that they correspond to the following formula:

(I")

*[chemical structure with $H_3C$, $R_2$, $R_4$, $R_1$, CN substituents]* in which:

$R_1$ denotes an alkyl having from 1 to 16 carbon atoms or an allyl group;

$R_2$ denotes an alkyl having from 1 to 8 carbon atoms;

$R_4$ denotes a halogen atom, a hydrogen atom, an alkoxy radical having from 1 to 6 carbon atoms or a radical

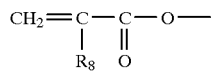

with $R_8$ denoting H or $CH_3$.

6. Compounds according to claim 5, characterized in that, in formula (I"):

$R_1$ denotes a methyl, hexadecyl or allyl radical;

$R_2$ denotes a methyl or ethyl radical;

$R_4$ denotes a hydrogen atom, a chlorine atom, a methoxy radical or a radical $CH_2$=CH—COO—.

7. Process for the preparation of the compounds as defined in any of claims 2, 4, 5, 6, characterized in that it comprises the condensation of a Fischer base with an ortho-aminophenol substituted in position 4 with a group $R_6$ in a solvent medium in the presence of an oxidizing agent.

8. Process for the preparation of the compound of claim 1 comprising the condensation of a Fischer base, of formula:

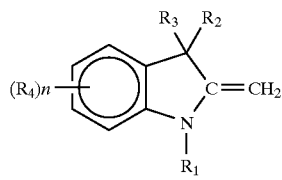

(II)

in which $R_1$, $R_2$, $R_3$, $R_4$ and n have the same meanings indicated in claim 1, with an annelated ortho-aminophenol of formula:

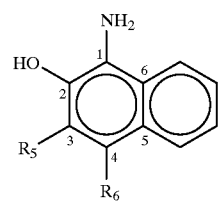

(III)

where $R_5$ and $R_6$ have the same meanings indicated above, in a solvent medium in the presence of an oxidizing agent.

9. Composition for applying to or introducing into a transparent organic polymer, wherein the composition contains at least one photochromic compound as defined in any of claims 3, 4, 5, 6, 1 or 2, in amounts which are sufficient to allow the material exposed to ultraviolet radiation to change color.

10. Composition for applying to or introducing into a transparent organic polymer, wherein the composition contains at least one photochromic compound as defined in claim 1, in amounts which are sufficient to allow the material exposed to ultraviolet radiation to change color; and wherein the composition is in liquid form containing, in dissolved or dispersed form, the at least one photochromic compound in a medium based on solvents which are suitable to be applied or to be introduced into a transparent polymer.

11. Composition for applying to or introducing into a transparent organic polymer, wherein the composition consists of a colorless or transparent solution based on polymers, on copolymers or on a mixture of transparent polymers in a suitable organic solvent, containing at least one photochromic compound as defined in any of claims 3, 4, 5, 6, 1 or 2, in amounts which are sufficient to allow the material exposed to ultraviolet radiation to change color.

12. Transparent solid material which is suitable for producing ophthalmic lenses, characterized in that it contains, on the surface and/or inside, at least one photochromic compound as defined in any of claims 3, 4, 5, 6, 1 or 2, in amounts which are sufficient to allow the material exposed to ultraviolet radiation to change color.

13. Transparent solid material according to claim 12, characterized in that it contains from 0.07 to 20% by weight of photochromic compounds.

14. Transparent solid material or composition for applying to or introducing into a transparent organic polymer, wherein the composition contains at least one photochromic compound as defined in claims 3, 4, 5, 6, 1, or 2, in amounts which are sufficient to allow the material exposed to ultraviolet radiation to change color; and wherein the at least one photochromic compound is used in conjunction with other photochromic compounds giving rise to different colorations.

15. Transfer varnish, characterized in that it contains at least one compound as defined in any of claims 3, 4, 5, 6, 1, or 2.

* * * * *